United States Patent [19]

Asayama et al.

[11] Patent Number: 4,594,139
[45] Date of Patent: Jun. 10, 1986

[54] AIR/FUEL RATIO DETECTOR

[75] Inventors: Yoshiaki Asayama, Hyogo; Tetsusyo Yamada; Shintaro Hirate, both of Aichi, all of Japan

[73] Assignees: Mitsubishi Denki Kabushiki Kaisha; NGK Spark Plug Co., Ltd., both of Japan

[21] Appl. No.: 681,335

[22] Filed: Dec. 13, 1984

[30] Foreign Application Priority Data

Dec. 15, 1983 [JP] Japan ................................. 58-237620

[51] Int. Cl.$^4$ ............................................ G01N 27/58
[52] U.S. Cl. ................................... 204/410; 204/406; 204/412; 204/425
[58] Field of Search ............... 204/412, 410, 424, 425, 204/426, 427, 428, 429, 1 S, 406; 60/276; 123/489

[56] References Cited

U.S. PATENT DOCUMENTS

| | | | |
|---|---|---|---|
| 4,224,113 | 9/1980 | Kimura et al. | 204/1 T |
| 4,264,425 | 4/1981 | Kimura et al. | 204/412 |
| 4,298,573 | 11/1981 | Fujishiro | 204/412 X |
| 4,450,065 | 5/1984 | Yamada et al. | 204/412 |

Primary Examiner—G. L. Kaplan
Attorney, Agent, or Firm—Sughrue, Mion, Zinn, Macpeak, and Seas

[57] ABSTRACT

An air/fuel ratio detector for use in measuring or controlling oxygen concentration in exhaust gas from a combustion device, comprising a plurality of solid electrolyte, oxygen ion conducting elements and an electronic control unit. The detector output, which is different over a wide range of air/fuel ratios, from fuel-rich to fuel-lean, enables monitoring of engine operating conditions without having to know beforehand whether the air/fuel ratio is fuel-lean or fuel-rich, and may be used as a feedback control in an internal combustion engine.

15 Claims, 6 Drawing Figures

AIR/FUEL RATIO DETECTOR

BACKGROUND OF THE INVENTION

The present invention relates to an air/fuel ratio detector for use in the measurement or control of the concentration of oxygen in exhaust gas from a combustion device such as an internal combustion engine or gas burner.

An oxygen sensor comprising an ion-conductive solid electrolyte (e.g. stabilized zirconia) coated with porous electrode layers (e.g. Pt porous layers) is capable of detecting combustion at a near theoretical (or stoichiometric) air/fuel ratio by sensing a change in electromotive force that is produced by the difference between the partial oxygen pressure of the exhaust gas and that of atmospheric air. This type of oxygen sensor is presently used in several applications, for example, in an automobile to run its internal combustion engine at the theoretical air/fuel ratio.

The conventional oxygen sensor produces a great change in its output if the operating air/fuel ratio (A/F ratio), which is the weight ratio of air to fuel, is at the theoretical value of 14.7, but otherwise the resulting change in output is negligible. Therefore, the output from this sensor cannot be effectively used if the engine is operating at A/F ratios other than the theoretical value.

Japanese Published Unexamined Patent Application (OPI) No. 153155/1983 discloses an oxygen concentration detector comprising a pair of oxygen ion conductive, solid electrolyte plates, each plate having an electrode layer on both sides, in a selected area close to one end. The two plates are positioned parallel to each other and spaced so as to leave a gap in an area corresponding to that selected area having the electrode layers. One electrolyte plate is used as an oxygen pump element, and the other plate is used as an electrochemical cell element that operates by the difference in oxygen concentration between the ambient atmosphere and the atmosphere in the gap between the two plates.

This type of detector features quick response, but according to the experiments conducted by the present inventors, if this device is used in a fuel-rich region having an A/F ratio lower than the theoretical 14.7, the direction of the resulting output is the same as that obtained in a fuel-lean region. Because a single output could signify more than one A/F ratio, the sensor can be used only when it is definitely known whether the combustion device to be controlled is operating in the fuel-rich or fuel-lean region.

Furthermore, it has been found that it is very difficult to use the detector at a theoretical air/fuel ratio or at a near region thereof with an accurate control of a combustion device and a quick response.

SUMMARY OF THE INVENTION

Accordingly, one object of the present invention is to provide an air/fuel ratio detector that is capable of detecting accurately the operating A/F ratio of a combustion device, such as an internal combustion engine, whether the ratio is fuel-rich, fuel-lean, or theoretical (i.e. 14.7), with a quick response.

Another object of the present invention is to provide an air/fuel ratio detector that enables a precise and simple feedback control in the above described ratio regions.

The objects of the present invention can be accomplished by an air/fuel ratio detector comprising an electrochemical cell element actuated by a difference in oxygen concentration, an oxygen pump element, and an oxygen sensor element, each element being in the form of an oxygen ion conductive solid electrolyte having a porous electrode formed on both sides, said electrochemical cell element facing one side of said pump element and positioned a small distance away, said sensor element facing the other side of said pump element to form therebetween an air compartment open to the atmosphere, said detector providing an output signal, whose magnitude is a function of the air/fuel ratio, corresponding to either the electromotive force of said electrochemical cell element or a pump current flowing through said pump element, in reference to the electromotive force generated by said sensor element.

Because of the arrangement recited above, the detector of the present invention has the advantage of requiring only one sensor probe in order to detect accurately the A/F ratio over all or part of a given combustion device's operating range, including the fuel-rich and fuel-lean ratios.

PREFERRED EMBODIMENT OF THE INVENTION

Figure 1:
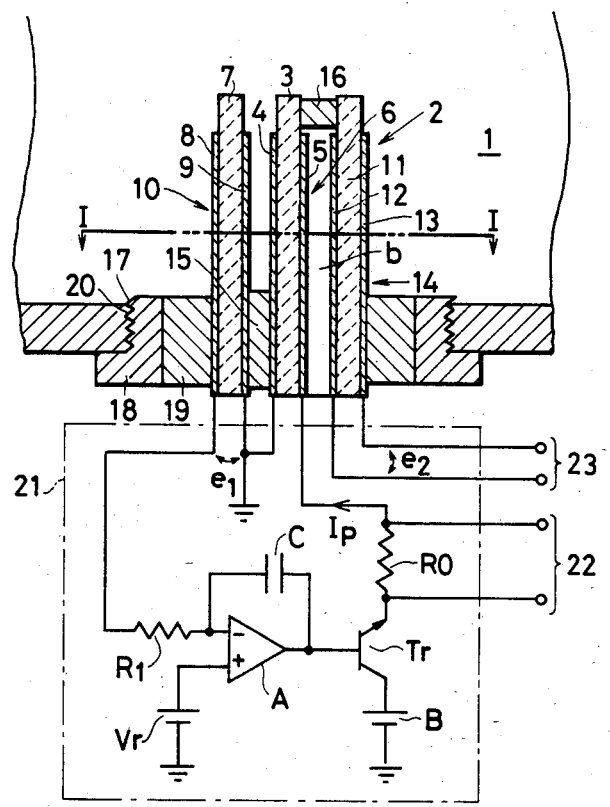
FIG. 1 is a layout for the air/fuel ratio detector according to one embodiment of the present invention.

The A/F ratio detector according to one preferred embodiment of the present invention is hereunder described with reference to the accompanying drawings. The detector is mounted in an exhaust pipe 1 in an internal combustion engine, as shown in FIG. 1. The probe 2 of the detector comprises a solid electrolyte oxygen pump element 6, a solid electrolyte, oxygen concentration difference actuated electrochemical cell element 10, and a solid electrolyte oxygen sensor element 14.

The pump element 6 consists of an ion conductive, solid electrolyte plate 3 (approx. 0.5 mm thick and preferably made of stabilized zirconia) having a porous platinum electrode layer 4 formed on one side and another porous platinum electrode layer 5 formed on the other side. Each Pt layer 4, 5 is about $20\mu$ thick and may be formed by a thick-film deposition technique. The electrochemical cell element 10 also consists of an ion conductive, solid electrolyte plate 7 (approx. 0.5 mm thick and preferably made of satiblized zirconia) having a porous platinum electrode layer 8 formed on one side and another porous Pt electrode layer 9 formed on the other side. Again, both Pt layers 8, 9 have a thickness of about 20μ and may be formed by a thick-film deposition technique. The sensor element 14 also consists of an ion conductive, solid electrolyte plate 11 having a porous Pt electrode layer 12 formed on one side and another porous Pt electrode layer 13 formed on the other side. The thickness and the material of the electrolyte plate 11 are preferably the same as in the case of the cell element 10 and the pump element 6, and the Pt layers 12 and 13 may also be formed by a thick-film deposition technique.

The pump element 6 and the electrochemical cell element 10 are positioned side by side in the exhaust pipe 1, with a small gap a (see FIG. 2) about 0.1 mm or less between them, and are held together by filling the gap at the detector's base portion with a heat-resistant insulating spacer 15, which may be an adhesive filler. The pump element 6 and the sensor element 14 are disposed in such a manner that the porous Pt electrode layers 5 and 12 face each other to define an air compartment b open to the atmosphere (see FIG. 2), and the two elements are held together in an air-tight manner by a heat-resistant spacer 16 provided in all parts of the gap except for the base portion.

A support 18 with a male thread 17 is fixed around the base portion of the combined pump element 6, electrochemical cell element 10 and sensor element 14 by means of a heat-resistant insulating adhesive member 19. The probe 2 is securely mounted in the exhaust pipe 1 by causing the male thread 17 to engage a female thread 20 in the exhaust pipe 1.

The A/F ratio detector having the construction shown above may be most advantageously fabricated by the following procedure: A green sheet of the spacer 16, preferably made of a ceramic, is put between green sheets for pump element 6 and sensor element 14, to each of which a paste of electrode material has been applied. After the green sheets have been pressed together, the resulting assembly is sintered to form a tubular member, including the pump element 6 and sensor element 14. This tubular member is then bonded to a sintered tubular cell element 10 by a heat-resistive ceramic adhesive.

An example of an electronic control unit for use in the detector of the present invention is shown in FIG. 1 by the reference numeral 21. The electromotive force (EMF) $e_1$, generated between the porous Pt electrode layers 8 and 9 on the electrochemical cell element 10, is applied to the inverting input terminal of an operational amplifier A through a resistor $R_1$, and the amplifier produces an output proportional to the difference between the EMF $e_1$ and a reference voltage $V_r$ applied to the non-inverting input terminal of the amplifier.

The output of the amplifier drives a transistor Tr to control the pump current $I_p$ flowing between the Pt electrode layers 4 and 5 on the pump element 6 in such a manner that $I_p$ is sufficient to maintain the EMF $e_1$ at a constant level $V_r$. The control unit 21 also includes a resistor $R_0$ to provide an output terminal 22 with an output signal corresponding to the pump current $I_p$ being supplied from a d.c. source B. The output of the amplifier A and its inverting input are connected by a capacitor C.

The control unit 21 also includes an output terminal 23 for outputting the electromotive force $e_2$ that is generated by the sensor element 14 in response to the difference in oxygen concentration between the atmosphere in the exhaust pipe 1 and the ambient atmosphere.

Figure 2:
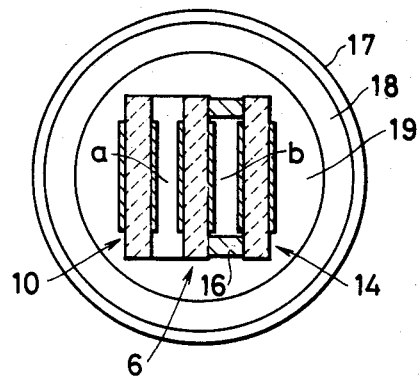
FIG. 2 is a cross-section taken along the line I—I of FIG. 1.
Figure 3:
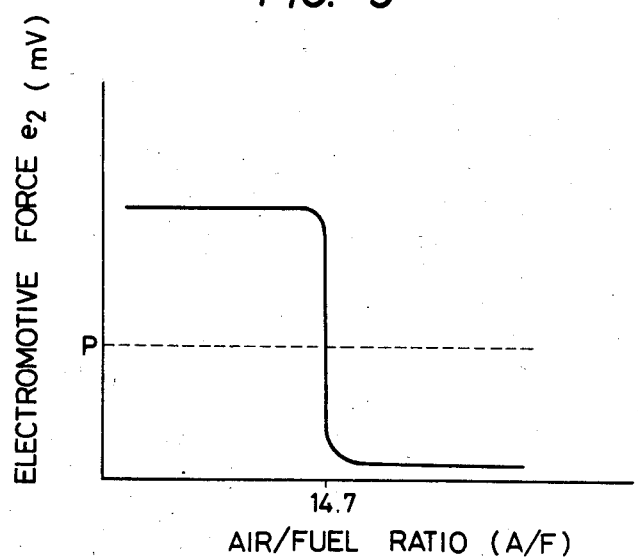
FIG. 3 is a characteristic curve showing A/F ratio vs. electromotive force $e_2$.
Figure 4:
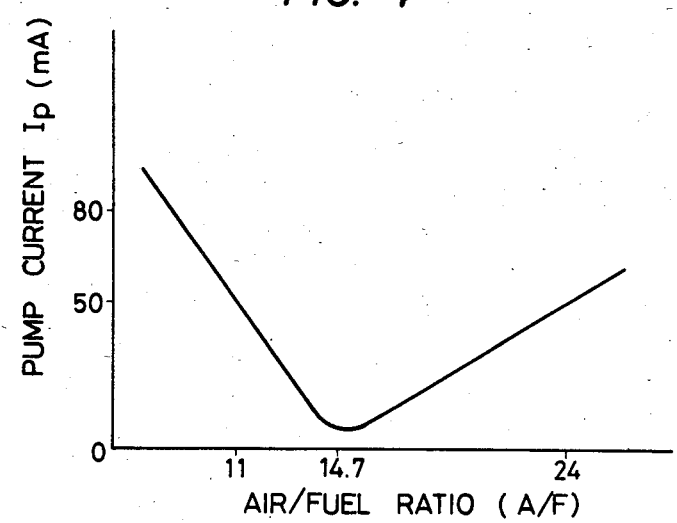
FIG. 4 is a characteristic curve showing the A/F ratio vs. the pump-out current $I_p$, flowing through the pump element for a constant level of the electromotive force $e_1$, of an oxygen concentration difference actuated electrochemical cell element.

Two characteristic curves for the detector shown in FIGS. 1 and 2 are illustrated in FIGS. 3 and 4. FIG. 3 shows the profile of electromotive force $e_2$ vs. A/F ratio. In the fuel-rich region where the operating A/F ratio is less than the theoretical 14.7, the detector produces a constant level of EMF $e_2$. This level suddenly drops at an A/F ratio of about 14.7, and in the fuel-lean region where the operating A/F ratio is greater than the theoretical value, the EMF produced is almost constant. FIG. 4 shows the profile of A/F ratio vs. $I_p$ for a reference voltage $V_r$ of, say, 60 mV. When the electromotive force $e_1$ is at 60 mV, $I_p$ decreases as the A/F ratio increases in the fuel-rich region and increases as the A/F ratio increases in the fuel-lean region.

The output terminal 23 for detecting EMF $e_2$ is so designed that the detector senses both fuel-richness and fuel-leanness, comparing EMF $e_2$ to P, which is a preselected reference point between maximum and minimum EMF levels.

When the engine is running in the fuel-rich region, the EMF $e_2$ of the sensor element 14 must be greater than P, and this information and an output signal corresponding to the resultant pump current $I_p$ flowing through the pump element 6 may be detected so as to measure the operating A/F ratio for the fuel-rich region. If the engine is operating in the fuel-lean region, the EMF $e_2$ of the sensor element 14 must be smaller than P, and this information and an output signal corresponding to the resulting pump current $I_p$ may be detected to determine the operating A/F ratio for the fuel-lean region.

The detector of the present invention having the construction described above enables accurate measurement of the operating A/F ratio of an engine over a wide range, including both the fuel-rich and fuel-lean values with a quick response. Consequently, this detector may be used as a feedback control over the A/F ratio, wherein a signal, corresponding to the present level of the A/F ratio, as detected by the probe 2 mounted in the exhaust pipe 1, is passed through a feedback loop to enable maintenance of the desired A/F ratio.

The proportional change of $I_p$ with A/F ratio in the fuel-lean region is already known and is disclosed in, for example, Japanese Published Unexamined Patent Application (OPI) No. 153155/1983. The partial pressure of oxygen in the exhaust gas introduced into the gap a is modified by the action of the pump element 6 to a value which differs from the partial pressure of the oxygen in the exhaust gas flowing through the pipe 1. The pump current $I_p$ supplied to the pump element 6 is controlled so that the electromotive force $e_1$ of the cell element 10, as produced in response to the differential partial oxygen pressure, is held constant. It has been found from experiments that since $e_1$ is constant, the pump current $I_p$ changes in proportion to the concentration of oxygen in the exhaust gas. Sensitivity of the detector to the presence of CO gas in the exhaust when the A/F ratio is fuel-rich would be the primary reason for this oxygen pump-out action.

Figure 5:
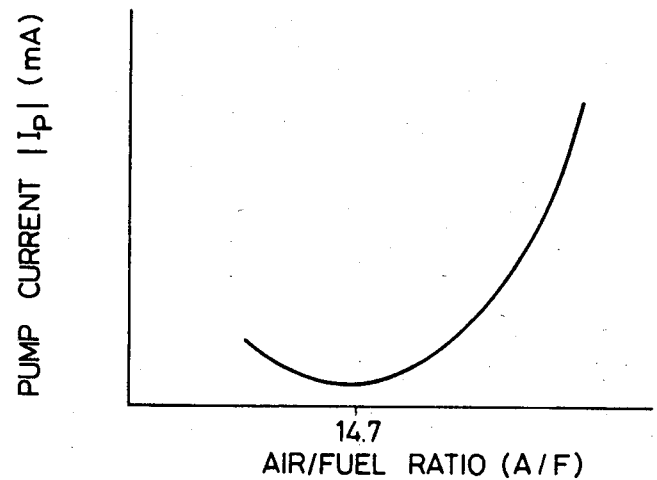
FIG. 5 is a characteristic curve showing the A/F ratio vs. the pump-in current $I_p$, flowing through the pump element for a constant level of the electromotive force $e_1$, of the electrochemical cell element.

In the embodiment shown above, the pump current $I_p$ is caused to flow through the pump element 6 in such a direction that oxygen is pumped out of the gap a into the exhaust pipe 1 ($I_p > 0$). If desired, the $I_p$ may be caused to flow in the opposite direction ($I_p < 0$) so that oxygen is pumped into the gap a from the air compartment b. FIG. 5 shows the profile of A/F ratio vs. $I_p$ in this modified case, with the output of the electrochemical cell element 10 being held constant. The characteristics shown in FIG. 5, which reflect a certain correlation between the operating A/F ratio and $I_p$, also may be used for detection in the present invention.

When the pump current $I_p$ flowing through the pump element 6 (whether oxygen is pumped into or out of the gap a) is held constant, the EMF $e_1$ generated by the electrochemical cell element 10 also varies with the A/F ratio. This correlation likewise may be used for detection in the present invention.

Figure 6:
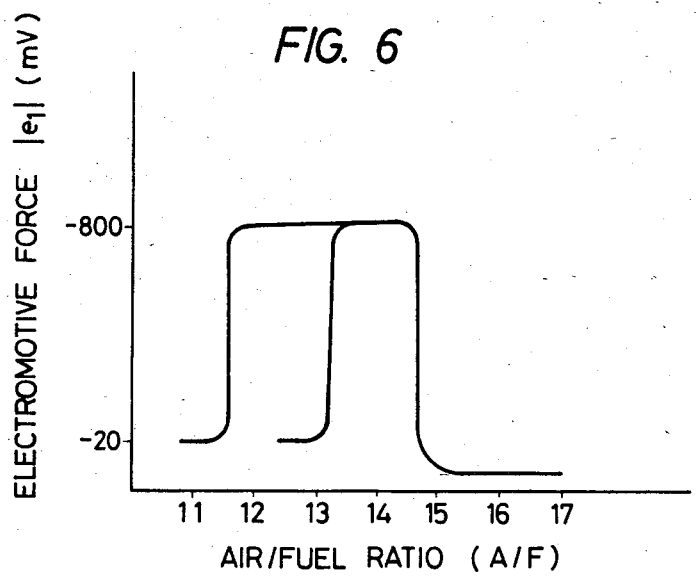
FIG. 6 is a characteristic curve showing the A/F ratio vs. the electromotive force $e_1$ of the cell element, with the pump-in current $I_p$ taken as a parameter.

FIG. 6 shows the profile of A/F ratio vs. the EMF ($e_1 < 0$) of the electrochemical cell element 10, with the oxygen pump-in current $I_p$ being taken as a parameter. As shown, sudden changes in the output occur in the fuel-rich region and at the theoretical A/F ratio. Varying the pump-in current $I_p$ affects the fuel-rich A/F ratio at which some of the abrupt changes in the EMF $e_1$ occur. This profile shows that the detector may be used in performing a precise and quickly responsive feedback control of the A/F ratio in the fuel-rich region.

More particularly, when an internal combustion engine is operating under such conditions that the A/F ratio should be fuel-rich, the characteristics shown in FIG. 6 corresponding to a constant pump-in current ($I_p < 0$) should be selected. If the operating conditions are such that the A/F ratio should be fuel-lean, the characteristics shown in FIG. 5 corresponding to a constant EMF ($e_1 < 0$) of the cell element 10 should be selected. By switching between these two modes as necessary, the desired continuous feedback control of the A/F ratio can be achieved over a combustion device's full operating range.

If it is necessary to maintain the A/F ratio at the theoretical 14.7, the EMF $e_2$ of the sensor element 14 may be used directly as a feedback control signal.

In the above described embodiments, each element is not heated by a heater. However, it is possible to achieve the present invention by providing a suitable heating means to each element.

In the detection probe of the present invention, the pump element and the cell element are provided side by side in the exhaust pipe with a small gap therebetween. As preferable embodiments they are fixed together by filling the gap at the base portions with a spacer. Thus, the gap formed between the pump element and the cell element is preferable to sufficiently open the peripheral edges to the exhaust gas so as to increase its response. However, the present invention is not limited to the configuration of open edges except for the base portions. For example, it is possible to provide a few support members between the solid-electrolyte plates of the pump element and cell element for more easily regulating the gap dimensions as far as the support member does not cause any considerable reduction of responsivity.

Also, the gap between the pump element and the cell element is preferably in a range from 0.01 to 0.15 mm. If the gap is too narrow, the response is reduced.

Of the electrodes of the respective elements, an electrode layer to define a small or fine gap is preferably a porous thick layer having a mean porosity of about 10-40% as determined by a porosimeter of the pressurized mercury type in consideration of its diffusion resistance against pertinent component gases such as oxygen gas.

Furthermore, in the case that the electrode layer is formed by a suitable thin-film deposition technique, it is preferable to, thereon, provide a porous layer such as a ceramic material which may be added with a catalytic agent for obtaining a catalytic action.

Thus, a highly-responsive detection probe can be readily manufactured by the above described conditions.

What is claimed is:

1. An air/fuel ratio detector for monitoring the concentration of a particular gas in the exhaust gas from a combustion device, said detector comprising:
    (a) first solid electrolyte sensing means for generating a first output signal indicating whether said concentration of said particular gas in said exhaust gas is above or below a predetermined value; and
    (b) second solid electrolyte sensing means for generating a second output signal indicating at least one specific value of said concentration above or below said predetermined value, whereby an air/fuel ratio across a range surrounding said predetermined value may be detected, said second solid electrolyte sensing means comprising:
        (i) a first solid electrolyte element with electrodes on both sides;
        (ii) a second solid electrolyte element with electrodes on both sides, positioned on one side of said first element, with a first gap between said second element and said first element; and
        (iii) means for producing electric current through said first element,
    said first element changing the level of said concentration in said first gap in accordance with said current for creating a constant first electromotive force between the electrodes of said second element.

2. An air/fuel ratio detector as claimed in claim 1, said first element increasing the level of said concentration in said first gap by pumping an amount of said particular gas into said first gap.

3. An air/fuel ratio detector as claimed in claim 1, said first element decreasing said level of concentration in said first gap by pumping an amount of said particular gas out of said first gap.

4. An air/fuel ratio detector as claimed in claim 1, said first solid electrolyte sensing means comprising:
    (i) a third solid electrolyte element with electrodes on both sides, positioned on the other side of said first element, with a second gap between said third element and said first element for receiving a reference gas,
    a second electromotive force being produced between the electrodes of said third element in accordance with the difference between the level of concentration of said particular gas in said exhaust gas and the level of concentration of said particular gas in said reference gas.

5. An air/fuel ratio detector as claimed in claim 4, wherein said reference gas is atmospheric air.

6. An air/fuel ratio detector as claimed in claim 5, wherein said particular gas is oxygen.

7. An air/fuel ratio detector for monitoring the concentration of a particular gas in the exhaust gas in an exhaust pipe of a combustion device, as claimed in claim 6, further comprising means for fixing said detector within said exhaust pipe, said second element being fastened to said first element with a heat-resistant insulating material, said third element being fastened to said first element in an air-tight manner with heat-resistant material, said second gap being open only at one of two ends of said detector, said open end being positioned farther away from the flow of said exhaust gas and facing away from said flow and toward atmospheric air.

8. An air/fuel ratio detector for monitoring the concentration of a particular gas in the exhaust gas from a combustion device, said detector comprising:
(a) first solid electrolyte sensing means for generating a first output signal indicating whether said concentration of said particular gas in said exhaust gas is above or below a predetermined value; and
(b) second solid electrolyte sensing means for generating a second output signal indicating at least one specific value of said concentration above or below said predetermined value, whereby an air/fuel ratio across a range surrounding said predetermined value may be detected, said second solid electrolyte sensing means comprising:
(i) a first solid electrolyte element with electrodes on both sides;
(ii) a second solid electrolyte element with electrodes on both sides, positioned on one side of said first element, with a first gap between said second element and said first element, said second element producing an output voltage in accordance with the difference in concentration of said particular gas at each of its electrodes; and
(iii) means for producing a substantially constant electric current through said first element for changing the level of said concentration in said first gap in accordance with said current, said second output signal changing in accordance with said output voltage of said second element.

9. An air/fuel ratio detector as claimed in claim 8, said second output signal undergoing an abrupt change in level at a first value of said concentration other than said predetermined value, said at least one specific value comprising a range of values between said first value and said predetermined value.

10. An air/fuel ratio detector as claimed in claim 8, said first element increasing the level of said concentration in said first gap by pumping an amount of said particular gas into said first gap.

11. An air/fuel ratio detector as claimed in claim 8, said first element decreasing the level of said concentration in said first gap by pumping an amount of said particular gas out of said first gap.

12. An air/fuel ratio detector as claimed in claim 8, said first solid electrolyte means comprising:
(i) a third solid electrolyte element with electrodes on both sides, positioned on the other side of said first element, with a second gap between said third element and said first element for receiving a reference gas,
a second electromotive force being produced between the electrodes of said third element in accordance with the difference between the level of concentration of said particular gas in said exhaust gas and the level of concentration of said particular gas in said reference gas.

13. An air/fuel ratio detector as claimed in claim 12, wherein said reference gas is atmospheric air.

14. An air/fuel ratio detector as claimed in claim 13, wherein said particular gas is oxygen.

15. An air/fuel ratio detector for monitoring the concentration of a particular gas in the exhaust gas in an exhaust pipe of a combustion device, as claimed in claim 14, further comprising means for fixing said detector within said exhaust pipe, said second element being fastened to said first element with a heat-resistant insulating material, said third element being fastened to said first element in an air-tight manner with heat-resistant material, said second gap being open only at one of two ends of said detector, said open end being positioned farther away from the flow of said exhaust gas and facing away from said flow and toward atmospheric air.

* * * * *